United States Patent
Ireland et al.

(10) Patent No.: US 6,494,892 B1
(45) Date of Patent: Dec. 17, 2002

(54) DISPOSABLE HUB FOR A SURGICAL CUTTING INSTRUMENT

(75) Inventors: Dan C. Ireland, Martinsville, IN (US); Craig L. Drager, Ballwin, MO (US); Michael E. Bisch, Kirkwood, MO (US); John J. Weidenbenner, Ballwin, MO (US)

(73) Assignee: Suros Surgical Systems, Inc., Indianapolis, IN (US)

( * ) Notice: Subject to any disclaimer, the term of this patent is extended or adjusted under 35 U.S.C. 154(b) by 0 days.

(21) Appl. No.: 09/335,153

(22) Filed: Jun. 17, 1999

Related U.S. Application Data

(63) Continuation of application No. 09/175,491, filed on Oct. 20, 1998.

(51) Int. Cl.[7] .............................................. A61B 17/14
(52) U.S. Cl. ..................... 606/180; 606/167; 606/79; 604/22
(58) Field of Search ................. 606/159, 167, 606/170, 171, 80, 79, 180, 107; 604/19, 22, 35

(56) References Cited

U.S. PATENT DOCUMENTS

| | | | |
|---|---|---|---|
| 4,314,560 A | | 2/1982 | Helgott et al. |
| 4,577,629 A | | 3/1986 | Martinez |
| 4,662,869 A | | 5/1987 | Wright |
| 4,696,298 A | | 9/1987 | Higgins et al. |
| 4,705,038 A | * | 11/1987 | Sjostrom et al. ............ 606/180 |
| 4,911,161 A | | 3/1990 | Schechter |
| 5,112,299 A | * | 5/1992 | Pascaloff ..................... 606/180 |
| 5,411,513 A | | 5/1995 | Ireland et al. |
| 5,492,527 A | | 2/1996 | Glowa et al. |
| 5,569,256 A | * | 10/1996 | Vaughn et al. ................ 606/80 |
| 5,601,583 A | | 2/1997 | Donahue et al. |
| 5,620,447 A | * | 4/1997 | Smith et al. .................. 606/79 |
| 5,676,680 A | | 10/1997 | Lim |
| 5,712,543 A | | 1/1998 | Sjostrom |
| 5,749,885 A | * | 5/1998 | Sjostrom et al. ............ 606/170 |
| 5,833,692 A | | 11/1998 | Cesarini et al. |

OTHER PUBLICATIONS

DYONICS,, "Leadership earned in the OR," Smith & Nephew Dyonics, Inc., (Oct. 20, 1991).

* cited by examiner

Primary Examiner—Glenn K. Dawson
(74) Attorney, Agent, or Firm—Rader, Fishman & Grauer, PLLC

(57) ABSTRACT

A surgical cutting instrument includes a hollow hub 15 that has a working portion 16 which terminates at a working end 17 and a connection portion 18 which terminates at a connection end. The connection portion 18 defines a cavity 20 and a lock member 22, which projects from an outer surface 21 of the connection portion 18. A surgical cutting element extends from the working end 17 and is operationally connected to a source of motion. A hollow hub connector 60 has a cylindrical wall 61 with a hand-piece connection portion 62 and a hub engagement portion 65. The hub engagement portion defines a chamber 70 for receiving the connection portion 18 of the hub 15. The chamber 70 has a longitudinal axis $A_1$ parallel to the length of the hub connector 60. The hub engagement portion 65 further defines a channel 75 through the cylindrical wall 61 for receiving the lock member 22. The channel is in communication with the chamber 70 and has a longitudinal section 76 defined along the length L of the connector. The channel also has a second transverse section 77 communicating with the longitudinal section 76 at a first end 78 and having a second opposite end 79. Further, the channel has a locking recess 81 defined in the wall 62 perpendicularly to the transverse section 77 and in communication with the opposite end 79 of the transverse section 77. The locking recess 81 is sized to receive the lock member 22. A spring element 100 urges the lock member 22 into the locking recess 81 when the locking member 22 is rotated into the opposite end 79 of the transverse section 77 of the channel 75.

11 Claims, 11 Drawing Sheets

DISPOSABLE HUB FOR A SURGICAL CUTTING INSTRUMENT

CROSS REFERENCE TO RELATED U.S. APPLICATION

This application is a continuation of U.S. application Ser. No. 09/175,491 filed Oct. 20, 1998.

FIELD OF THE INVENTION

The present invention relates to minimally invasive surgical instruments for the incision and removable of a wide range of tissues. Specifically, the invention concerns disposable surgical cutting assemblies for operative engagement with powered hand-pieces.

BACKGROUND OF THE INVENTION

Many medical treatments involve the removal of body tissues. In recent years, it has become standard to employ automated systems and less invasive surgical methods in order to achieve the best surgical outcome. Automated systems improve efficiency and effectiveness, particularly when the procedure requires cutting and removal of fibrous tissues that are difficult to completely sever. Minimally invasive surgical techniques avoid the trauma and expense of traditional surgical approaches because the site of pathology is accessed through portals rather than through a significant incision, thus preserving the integrity of intervening tissues. In some cases, these minimally invasive techniques require only local anesthesia, reducing post-operative recovery time and the risk of complications.

These recent improvements are particularly beneficial in the intricate, micro-surgical fields such as surgical ophthalmology and neurosurgery where extreme precision is essential, yet many of the tissues encountered can be fibrous. In these fields, surgical cutting probes are used to separate and remove pathologies from delicate structures. Fine discrimination and manipulation is required to avoid damaging healthy tissue. For example, certain conditions require the removal of tissue, such as vitreous, from the eye to preserve vision or maintain eye health. Removal of the vitreous is difficult due to the presence of fibers and the risk of serious complications, such as detachment of the inflexible, yet delicate, retina.

Since some of the fibers contained within the vitreous are attached to the retina, any incomplete cutting of the fibers could create retinal traction which could lead to retinal detachment. Incomplete cutting may result from a dull cutting blade, wherein the blade would merely pull the fibers and increase the retinal traction, or from a poor interface of the cutting edges of the outer needle and the cutting blade wherein the shearing effect of the edges passing across one another is reduced. In addition, imperfect alignment of the cutting blade within the outer tube could cause the shearing action to be localized at the center of the cutting edges and prevent the outer portion of the cutting edges from interfacing sufficiently close enough for a clean shearing action to occur.

Many of the known surgical tissue cutting instruments, for ophthalmology and other applications, employ the "tube within a tube" technology. These devices combine constant suction with a repeated cutting motion of a blade. Typically, an inner cutting sleeve is operated within the central bore of an outer cutting sleeve. The outer sleeve defines one or more apertures for receiving tissue when suction is applied. The inner sleeve can be reciprocated or rotated within the outer sleeve to pass a cutting edge past the aperture to cut tissue.

Although such automated cutters are a mayor advance in the art, several problems have been identified, such as incomplete cutting, clogging and the inability to cut harder tissues. Some of these problems arise from dull cutting blades or imperfect alignment of the blade within the outer tube. Over the years, many improvements to the basic tube within a tube design have been developed in an attempt to address these functional problems. While it has been a formidable challenge to address these problems while maintaining the minimally invasive features of the devices, some have been successful. An example of such an improvement is disclosed in U.S. Pat. No. 5,782,849 issued to Miller.

In addition to these functional issues, the risk of the transmission of infective agents must also be addressed. Disposable devices and/or sterilization procedures are employed. For example, disposable blades can be coupled with reusable, sterilizable hand-pieces. In some commercially available systems, the disposable surgical blades are connectable to a hand-piece through a locking collar, spring, and key and groove arrangement. Unfortunately, these arrangements are complicated and cumbersome, increasing the fiddle factor and risk of malfunction. Moreover, the locking collars and other components can become contaminated with tissue, preventing proper function of the connection mechanism.

Therefore, one problem that has remained unsatisfied in the art is the need for disposable surgical cutter components that provide convenient reasonable cost. Accordingly a need has remained for disposable surgical cutting components that can be easily and efficiently assembled and yet provide precision operation.

SUMMARY OF THE INVENTION

Briefly describing certain aspects of the invention, a surgical cutting instrument is disclosed. The instrument includes a hollow hub having a working portion, which terminates at a working end and a connection portion, which terminates at a connection end. The connection portion defines a cavity and a lock member which projects from an outer surface of the connection portion. An outer tubular member extends from the working end and is sized for insertion into an anatomical space. The outer tubular member defines a central bore along the length I of the outer tubular member. The outer tubular member has a proximal end attached to the working end of the hub and a distal end. The outer tubular member further defines a cutting opening adjacent the distal end and sized to receive tissue therethrough.

A cutting member is slidably disposed within the central bore of the outer tubular member. The cutting member has a first operational end, which defines a cutting head, and a second engagement end disposed within the cavity of the hub. A drive element is also disposed within the cavity and has a drive mount portion connected to the engagement end of the cutting member. The drive element further has a mating portion operationally connectable to a source of motion. The drive element translates motion from the source of motion to the cutting member to move the cutting member relative to the outer tubular member so the cutting head traverses the cutting opening. The instrument includes a powered hand-piece having a source of motion and an outer shell, which defines an outer gripping portion.

A hollow hub connector is provided within the handpiece. The connector has a cylindrical wall with a hand-piece connection portion and a hub engagement portion. The connection portion is disposed within and is connected to the hand-piece. The hub engagement portion defines a chamber for receiving the connection portion of the hub. The chamber has a longitudinal axis $A_L$ parallel to the length of the hub connector. The hub engagement portion further defines a channel through the cylindrical wall for receiving the lock member. The channel is in communication with the chamber. The channel has a longitudinal section defined in the wall parallel to the length L of the connector. The channel also has a second transverse section communicating with the longitudinal section. A locking recess is defined in the wall perpendicularly to the transverse section, and in communication with the opposite end of the transverse section. The locking recess is sized to receive the lock member.

Thus, the connection portion of the hub is slidable within the chamber along the longitudinal axis when the lock member is disposed within the longitudinal section of the channel. The connection portion of the hub is rotatable within the chamber when the lock member is disposed within the transverse section of the channel. The connection portion of the hub is fixed within the chamber when the lock member is disposed within the locking recess.

In another embodiment, the invention includes a spring element disposed on the connection portion of the hub. The spring element urges the lock member into the locking recess wherein the locking member is rotated into the opposite end of the transverse section of the channel. The spring element has a squeezed position when the lock member is in the transverse section of the channel and a rest position when the lock member is in the locking recess. In preferred embodiments, the spring element is a beam spring disposed at the connection end of the hub. The beam spring includes a beam having a first face adjacent the connection end and a second opposite face with a boss projecting from the opposite face.

In still another aspect of the invention, the instrument includes a drive connector disposed within the chamber of the hub connector. The drive connector is operably engageable to the source of motion and releasably matable to the mating portion of the drive element when the hub is engaged to the hub connector. In some embodiments, the mating portion includes a transverse bar disposed within the cavity of the hub and the drive connector includes a bayonet element matable to the transverse bar. The bayonet element has a pair of spaced arms each terminating in a hook. The bayonet element is configured to releasably receive the transverse bar when the hub is disposed within the chamber and the lock members received within the longitudinal channel. When the hub is rotated the locking member is disposed within the locking recess, the transverse bar is captured by the hooks to thereby operatively engage the inner tubular member to the source of motion.

Accordingly, it is one object of the invention to provide disposable surgical cutter assemblies for operative engagement with powered hand-pieces. These and other objects, advantages and features are accomplished according to the devices and methods of the present invention.

DESCRIPTION OF THE PREFERRED EMBODIMENTS

Figure 1:
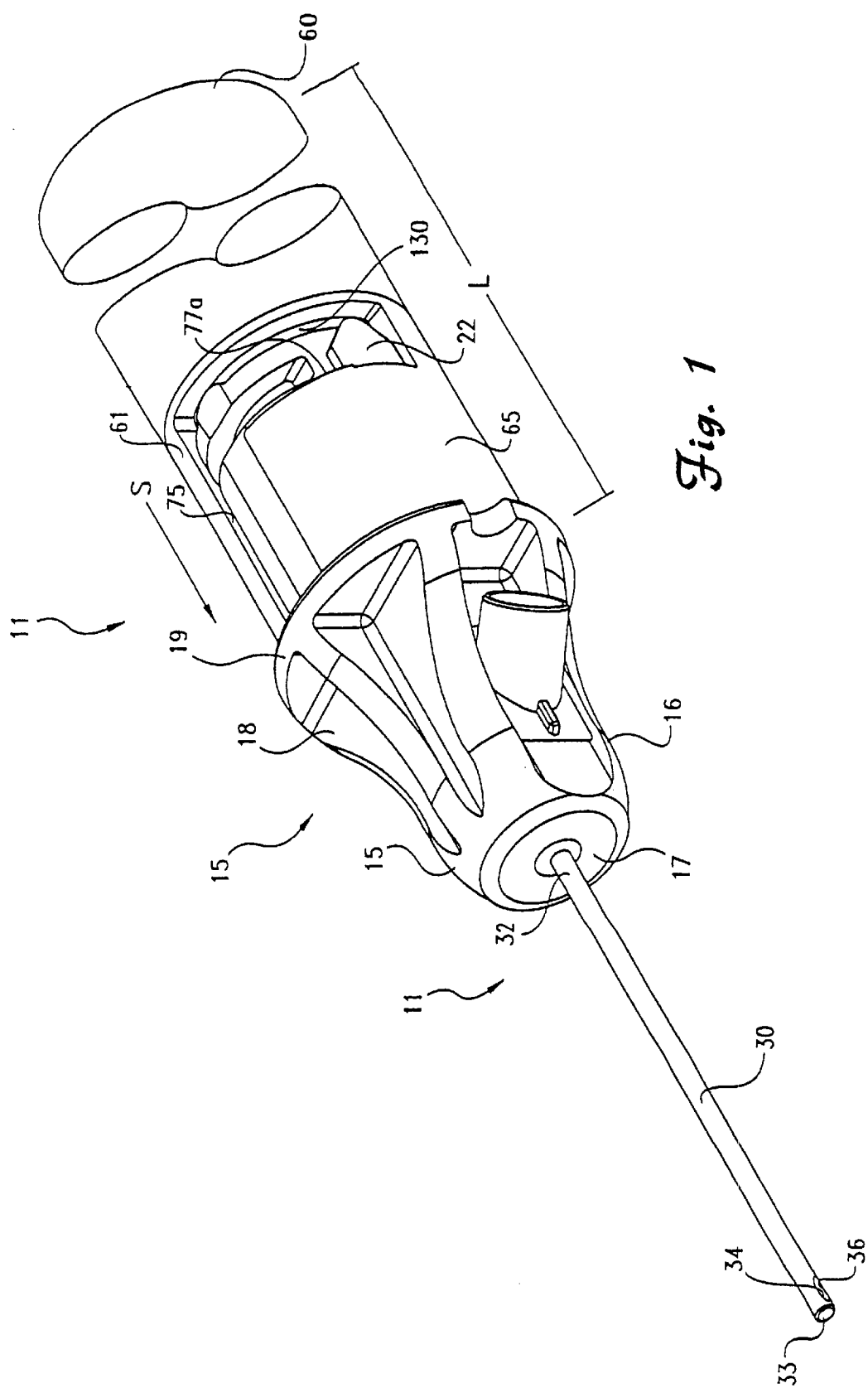
FIG. 1 is a side perspective view of one embodiment of a cutter assembly according to this invention.

For the purposes of promoting an understanding of the principles of the invention, reference will now be made to the embodiments illustrated in the drawings and specific language will be used to describe the same. It will nevertheless be understood that no limitation of the scope of the invention is thereby intended. The invention includes any alterations and further modifications in the illustrated devices and described methods and further applications of the principles of the invention which would normally occur to one skilled in the art to which the invention relates.

Figure 2:
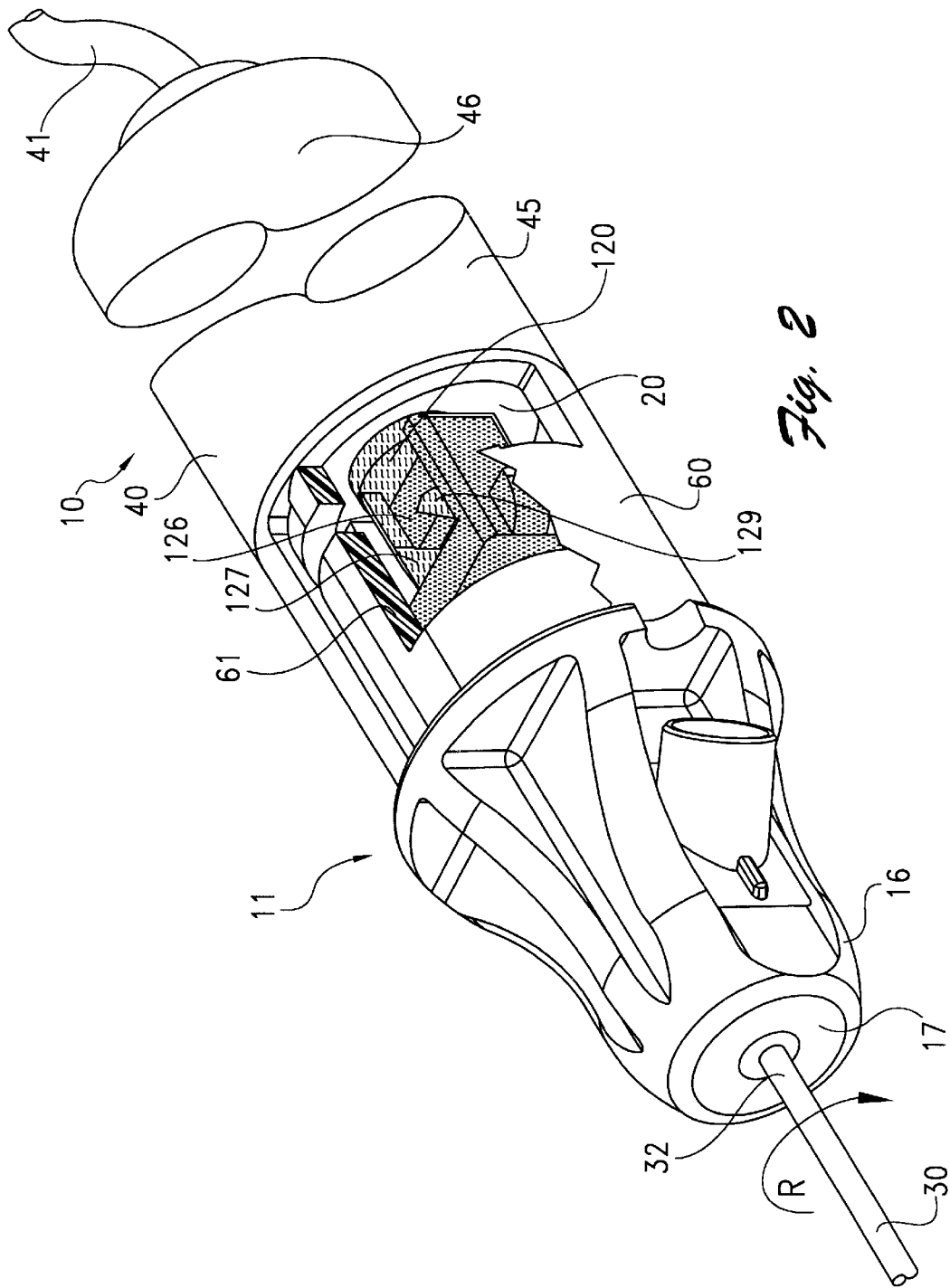
FIG. 2 is a partial sectional view of a surgical cutter including the hub assembly shown in FIG. 1.
Figure 3:
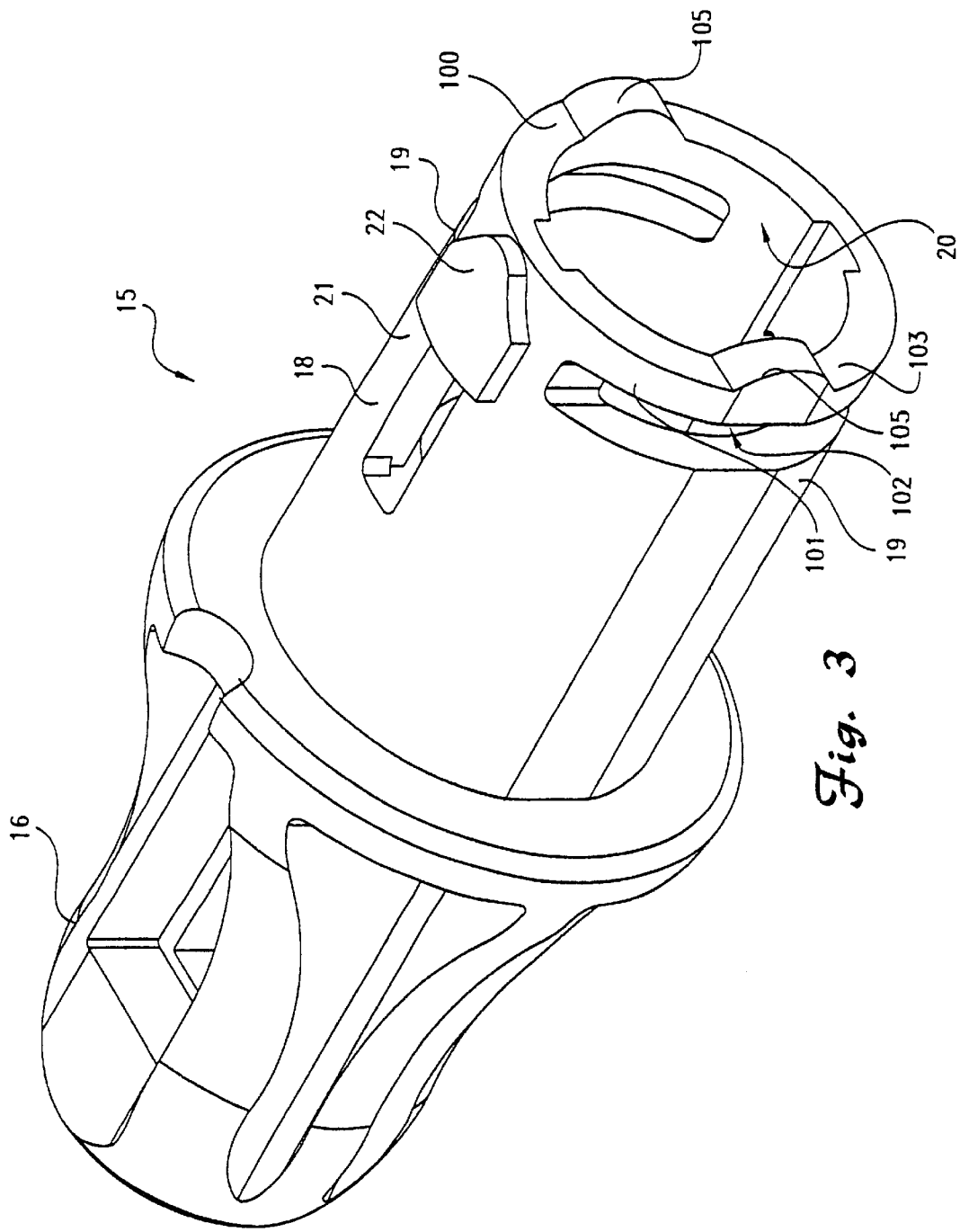
FIG. 3 is a perspective view of a hub according to one embodiment of this invention.

The present invention provides a surgical cutting instrument 10 in accordance with the preferred embodiment of the invention as depicted in FIGS. 1 and 2. In this embodiment the instrument 10 includes a disposable surgical cutting assembly 11 operatively connected to a powered hand-piece 40, which is connected to a source of power such as by electrical cable 41. The disposable assembly 11 includes a hollow hub 15 having a working portion 16 terminating at a working end 17 and a connection portion 18 terminating at a connection end 19 as depicted in FIG. 3. The connection portion 18 defines a cavity 20 and includes a lock member 22 projecting from an outer surface 21 of the connection portion 18.

Figure 4:
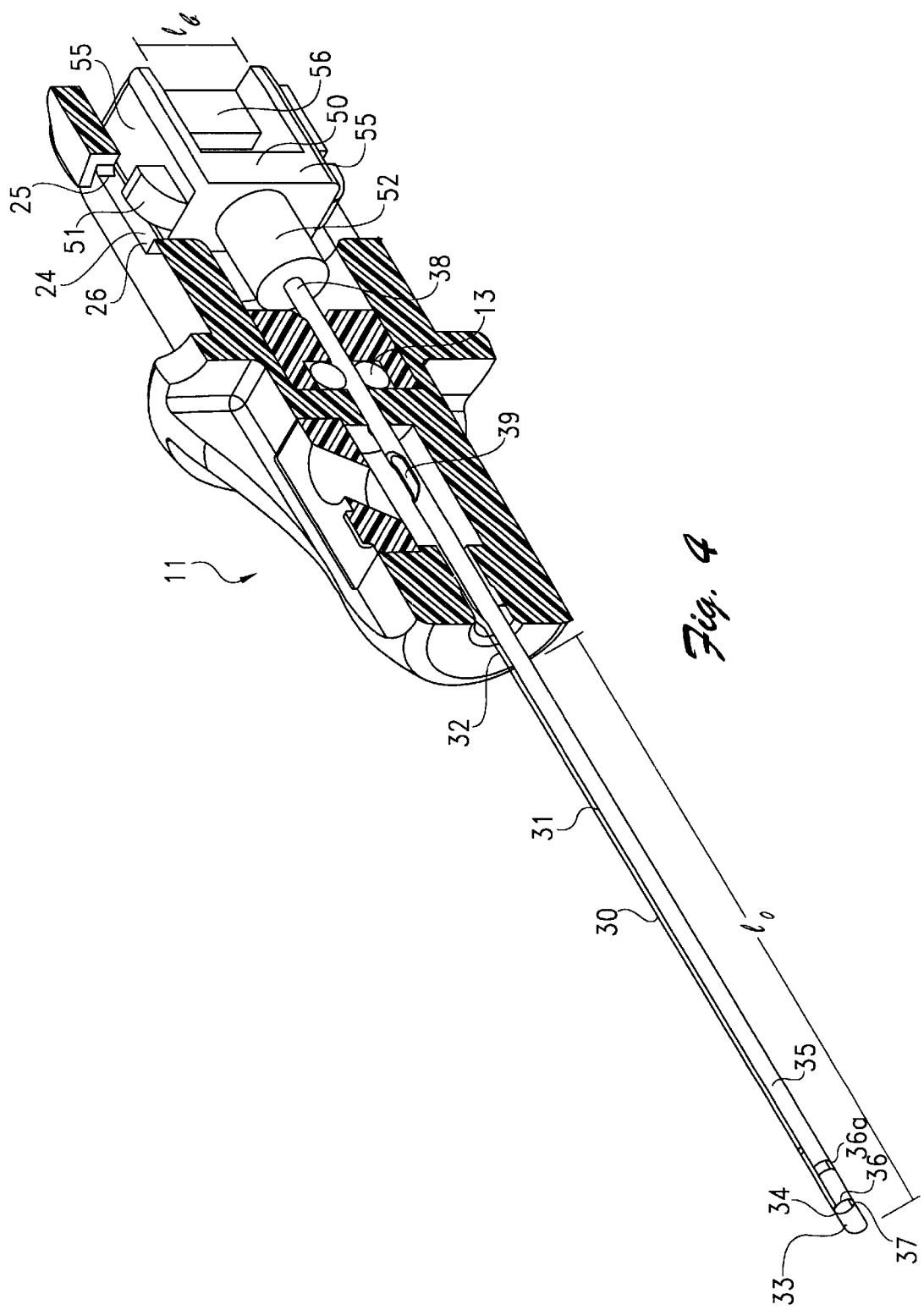
FIG. 4 is a side sectional view of a cutter assembly of this invention.

The disposable assembly 11 includes a disposable surgical cutting element In the particular embodiment shown in FIG. 1, the disposable surgical element includes a surgical cutter of the "tube within a tube" type such as the reciprocating and rotary cutters known in the art. Referring now to FIGS. 1 and 4, the disposable surgical cutting element includes an outer tubular member 30 sized for insertion into an anatomical space. The outer tubular member 30 defines a central bore 31 along the length I of the outer tubular member 30. The outer tubular member 30 has a proximal end 32 attached to the working end 17 of the hub 15 and a distal end 33. The outer tubular member 30 of this embodiment defines a cutting opening 34 adjacent the distal end 33 that is sized to receive tissue therethrough. In some embodiments, the cutting opening 34 has a first cutting edge, such as is disclosed in the Miller patent, U.S. Pat. No. 5,782,849, the entire disclosure of which is hereby incorporated by reference. In the particular embodiment depicted in FIG. 1, the cutting opening 34 is oval shaped; however, any suitably shaped cutting opening is contemplated by this invention.

In this embodiment, the surgical cutting element includes an inner tubular member or cutting member 35 slidably disposed within the central bore 31 of the outer tubular member 30. The cutting member 35 has a first operational end 36 defining a cutting head 37 and a second engagement end 38 disposed proximal to or within the cavity 20 of the hub 15. In preferred embodiments, the tubular members of this invention may have various features that enhance their function. For example, the inner tubular member 35 shown in FIG. 4 includes a hinge 36a connecting the cutting edge portion 37 to the body of the cutting member 35 to permit pivoting of the cutting head 37 relative to the rest of the cutting member 35. As the cutting member 35 moves relative to the outer tubular member 30, the cutting head 37 contacts tissue drawn into the cutting opening. Resistance from the tissue causes the cutting head 37 to pivot about the hinge to form an essentially zero clearance between the cutting head 37 and the cutting opening 34 of the outer tubular member 30, as is disclosed in U.S. Pat. No. 5,782,849 to Miller.

Figure 5:
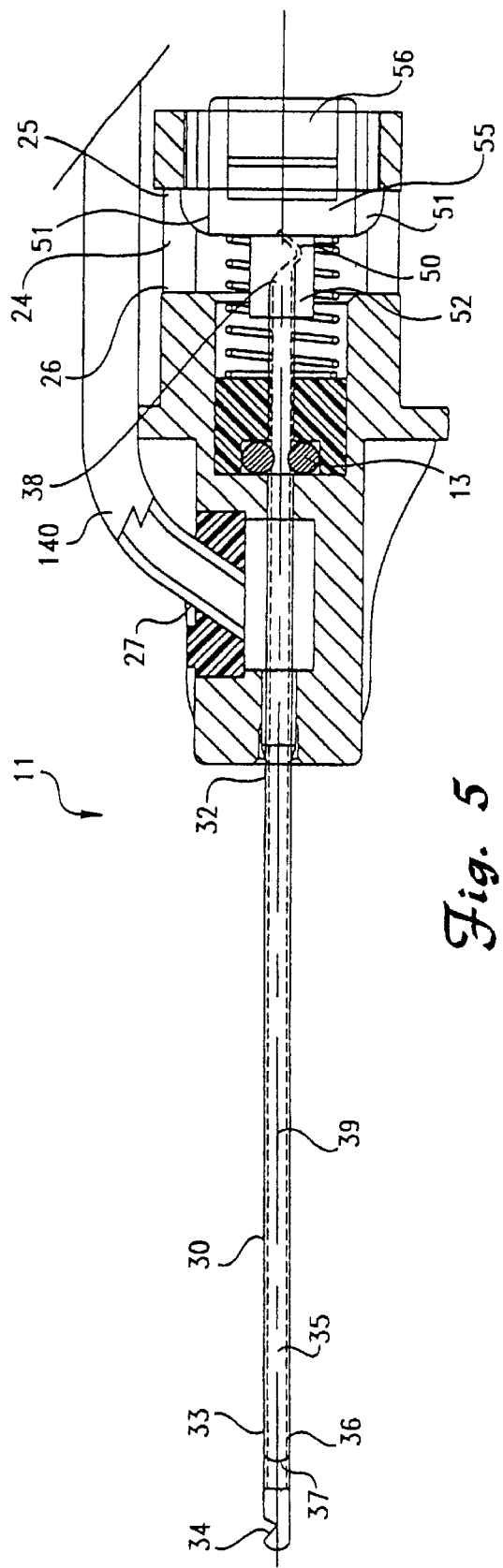
FIG. 5 is a side sectional view of a cutter assembly of this invention.

Referring now to FIGS. 4 and 5, the disposable assembly 11 also includes a drive element 50 disposed within the cavity 20 of the hub 15. The drive element 50 has a drive mount portion 52 connected to the engagement end 38 of the inner cutting member 35 and a mating portion 55 operationally connectable to a source of motion. The drive element 50 translates motion from a source of motion, such as a motor, to the cutting member 35 to move the cutting member 35 relative to the outer tubular member 30 so that the cutting head 37 traverses the cutting opening 34. In embodiments where the cutting opening 34 includes a cutting edge, the cutting edge of the cutting opening 34 is traversed by the cutting head 37. In the embodiments shown in FIGS. 4 and 5, the mating portion 55 includes a transverse bar 56 that is operatively matable to an element engaged to the source of mating. In this embodiment the drive element 50 is engaged to the hub by projections 51 that are positioned within slots 24 defined in the hub 15. In this embodiment, as the drive element 50 reciprocates and the projection 51 travels between the proximal end 25 and the distal end 26 of the slot 24.

Figure 6:
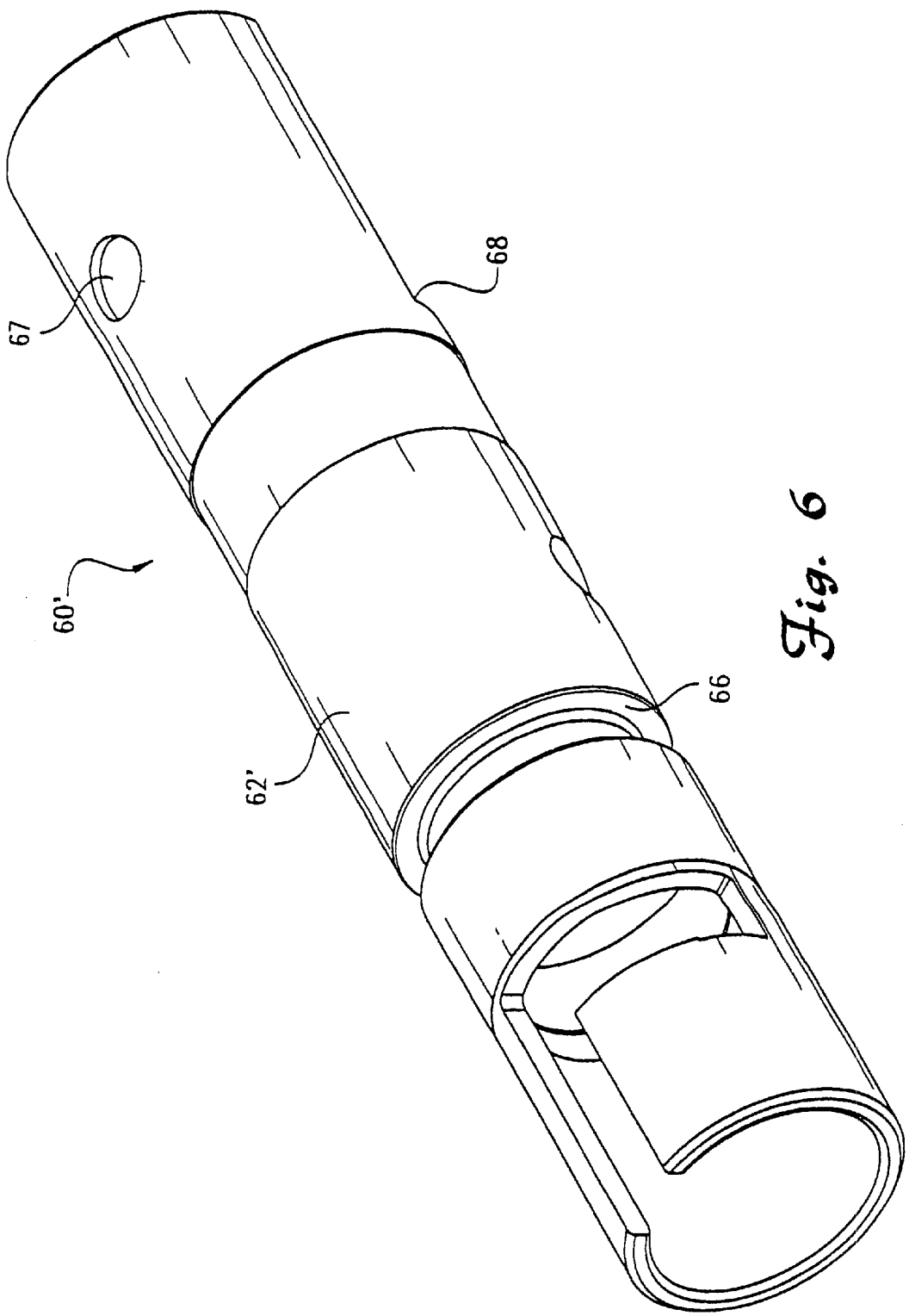
FIG. 6 is a perspective view of one embodiment of a hub connector.
Figure 7:
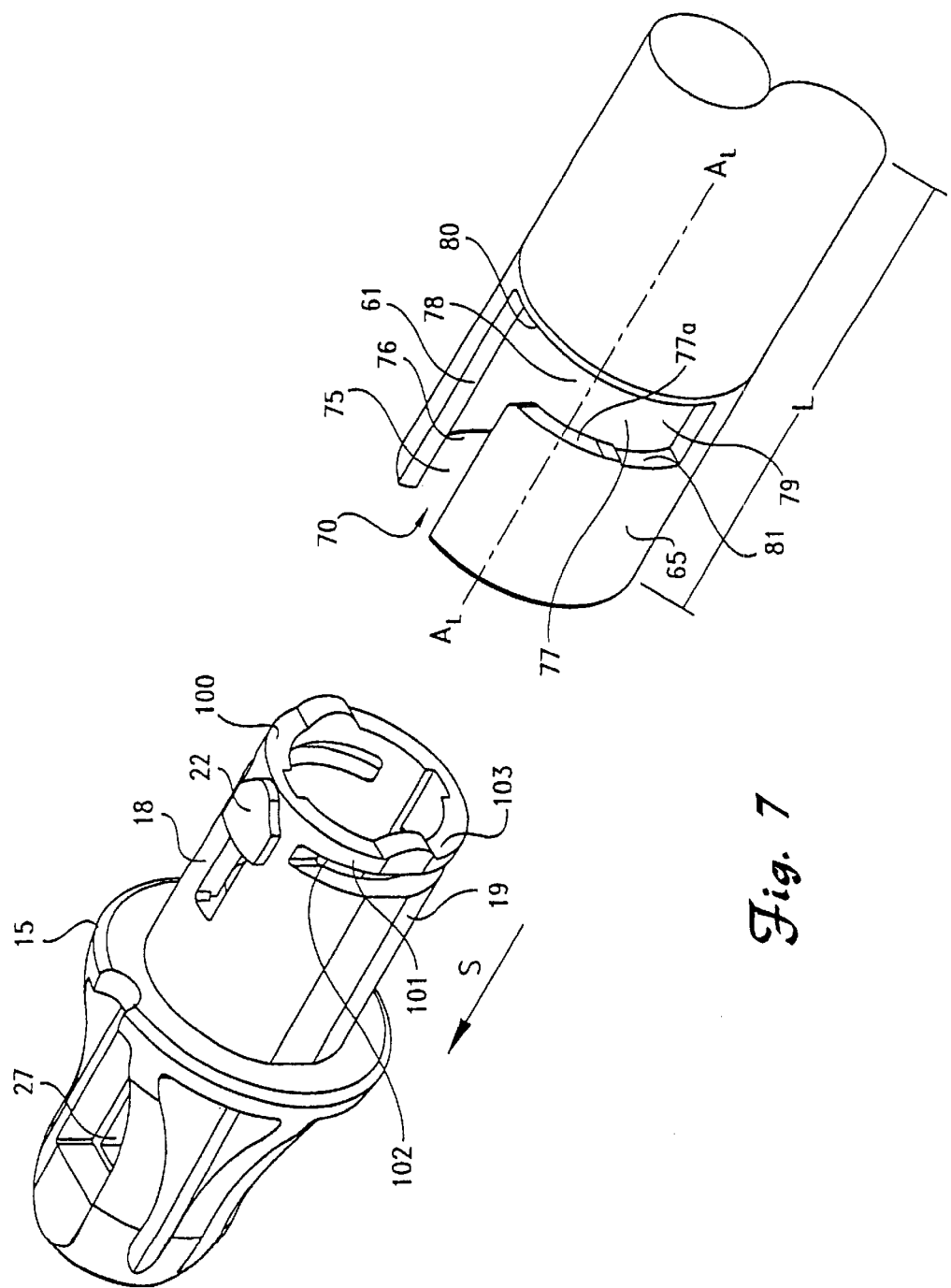
FIG. 7 is an exploded perspective view of a hub and connector assembly according to one embodiment of this invention.

In a preferred embodiment, the disposable surgical cutting assembly 11 also includes a hollow hub connector 60 having a length L and a cylindrical wall 61 as shown in FIGS. 2 and 6. The hub connector 60 includes, in some embodiments, a hand-piece connection portion 62 that is the hand-piece 40 or preferably, is insertable into a shell 45 having a gripping portion 46 to form the hand-piece. Referring now to FIG. 7, the hub connectors of this invention may include hand-piece connection portions 62' that have various features 66, 67, 68 that facilitate engagement of the hub connector 60' to the hand-piece 40 or the shell 45.

Figure 8:
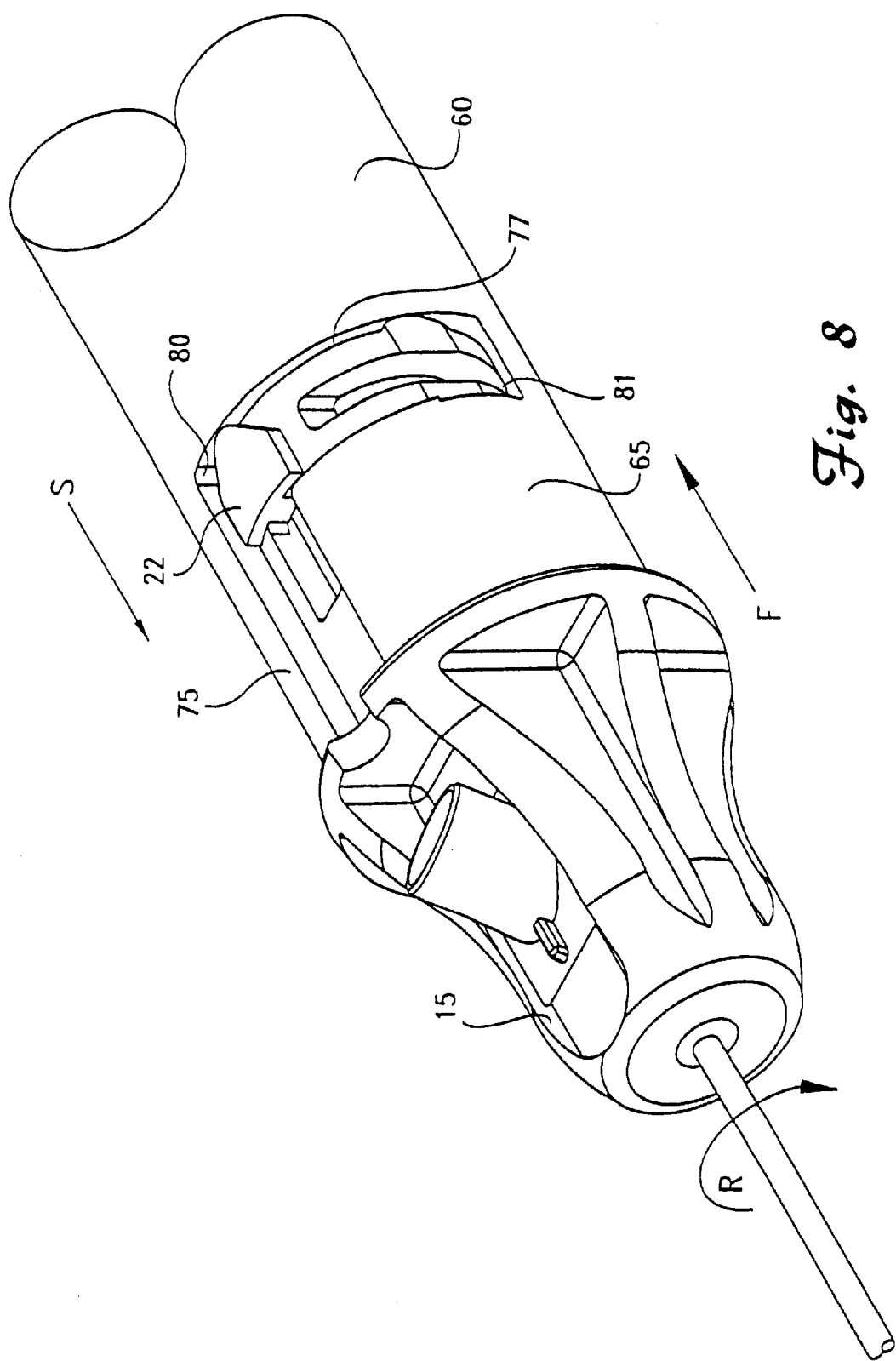
FIG. 8 is a side perspective view of a cutter assembly of this invention with the locking member of the hub at the junction of the longitudinal and transverse sections of the channel of the hub connector.

As shown in FIGS. 1, 7 and 8, the connector 60 also includes a hub engagement portion 65 defining a chamber 70 for receiving the connection portion 18 of the hub. The chamber 70 has a longitudinal axis $A_L$ that is parallel to the length L of the hub connector 60. The hub engagement portion 65 further defines a channel 75 through the cylindrical wall 61 for receiving the lock member 22 when the hub 15 is disposed within the chamber 70. The channel 75 is in communication with the chamber 70 and has an essentially truncated J shape. Channel 75 has a first longitudinal section 76 defined along the length L of the connector 60. A second transverse section 77 communicates with the longitudinal section 76 at junction 80. The transverse section 77 has a first end 78 adjacent the junction 80 and an opposite second end 79. A locking recess 81 is defined through the wall 62 perpendicular to the transverse section 77 and communicates with the opposite end 79 of the transverse section 17. The locking recess 81 is sized to receive and retain the lock member 22. Of course, the particular size and configuration of the locking recess 81 will be determined by the configuration of the locking member 22 and the particular application of the disposable assembly 11. In general, the locking recess 81 is deep enough to retain the locking member 22 during operation of the instrument but shallow enough that the hub can be disengaged by hand It will be appreciated that the connection portion 18 of the hub 15 is slidable within the chamber 70 along the longitudinal axis $A_L$ of the chamber when the lock member 22 is disposed within the longitudinal section 76 of the channel 75. On the other hand, the connection portion 18 of the hub 15 is rotatable within the chamber 70, but not slidable along the axis $A_L$ when the lock member 22 is disposed within the transverse section 77 of the channel 75. Finally, the hub 15 is fixed relative to the hub connector 60 when the lock member 22 is disposed within the locking recess 81 as shown in FIG. 1.

Figure 9:
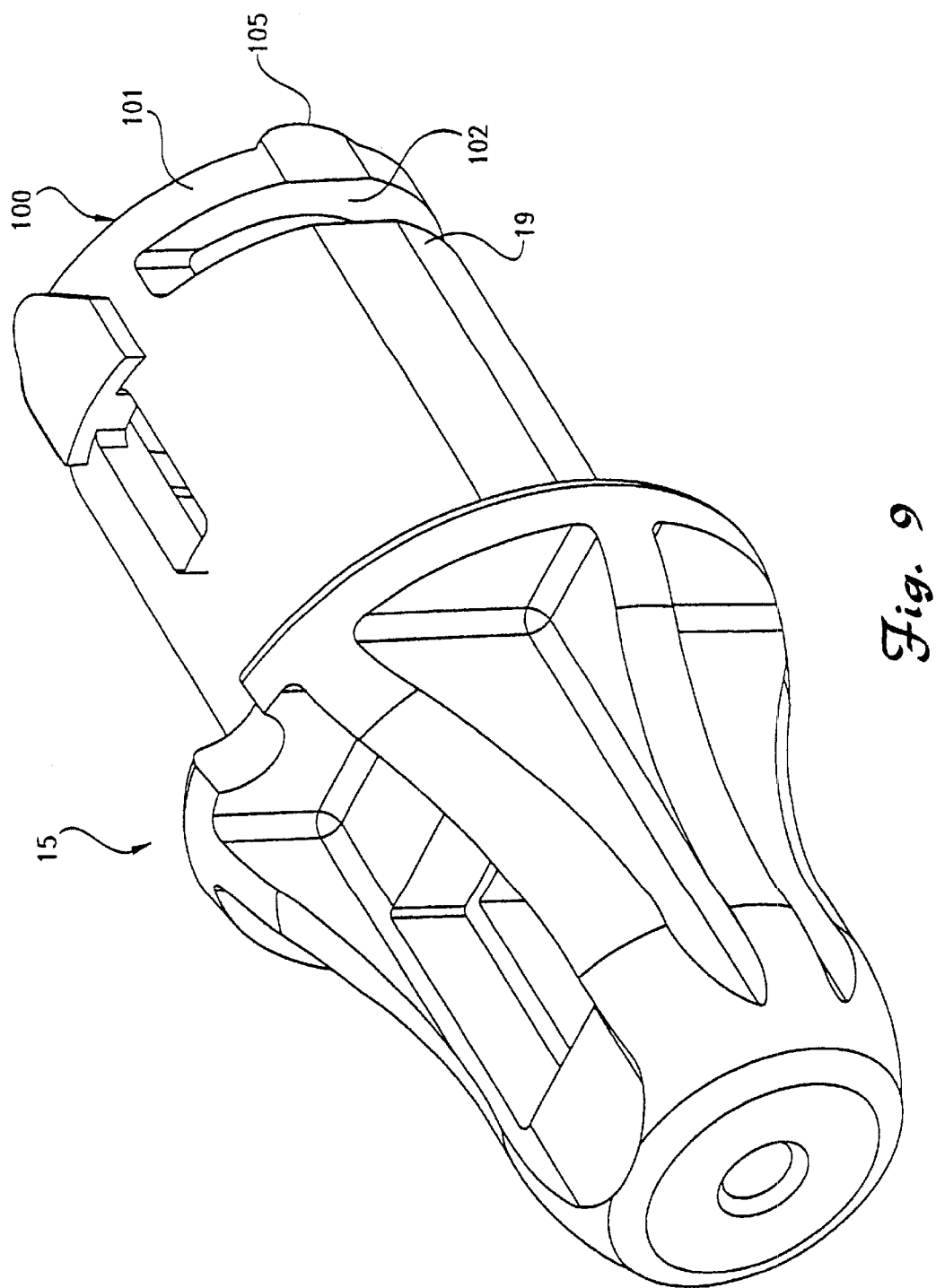
FIG. 9 is a perspective view of a hub according to one embodiment of this invention.

Referring again to FIGS. 1, 7 and 8, the disposable assembly 11 also preferably includes a spring element that operates to urge the lock member 22 into the lock member recess 81 when the locking member 22 is rotated into the opposite end 79 of the transverse section 77 of the channel 75. In preferred embodiments and as shown in FIGS. 3, 7 and 9, the spring element most preferably is a beam spring 100 disposed at the connection end 19 of the hub 15. The beam spring 100 includes a first beam 101 having a first face 102 adjacent the connection end 19 and a second opposite face 103. The spring element also includes a boss 105 projecting from the opposite face 103 of each of the beams 101. The spring element may include any number of beams 101 and the embodiments depicted include a pair of beams 101.

When the hub 15 is fully inserted into the chamber 70 of the hub connector 60 the lock member 22 bottoms out in the longitudinal section 76 of the channel 75 and the lock member is disposed within the junction 80 of the longitudinal section 76 and the transverse section 77. In this position, a force F must be exerted in the direction of the arrow F to depress the spring into the squeezed position so that the locking member 22 may enter the transverse section 77 of the channel 75. The boss 105 acts against a spring platform 130 disposed within the hub connector 60 or hand-piece 40. The spring platform is located at a spring-loaded distance from the transverse channel 77. The platform 130 can constitute a surface of the transverse channel 77 or can be a reduced diameter surface formed on wall 61, for example.

The spring element is resilient enough to be forced into a squeezed position when the lock member 22 is rotated into the transverse section 27 of the channel 75 and a force F is exerted to depress the spring. The force S of the spring is overcome by the action of the edge 23 of the lock member 22 on the trap surface 77a of the transverse section. When the hub 15 is further rotated within the chamber 70 so that the lock member 22 reaches the second end 79 of the transverse section 77 of the channel 75, the spring element forces the hub in the direction of the arrow S so that the spring element can assume a substantially at rest, or substantially unloaded, position with the lock member 22 and the locking recess 81.

Figure 10:
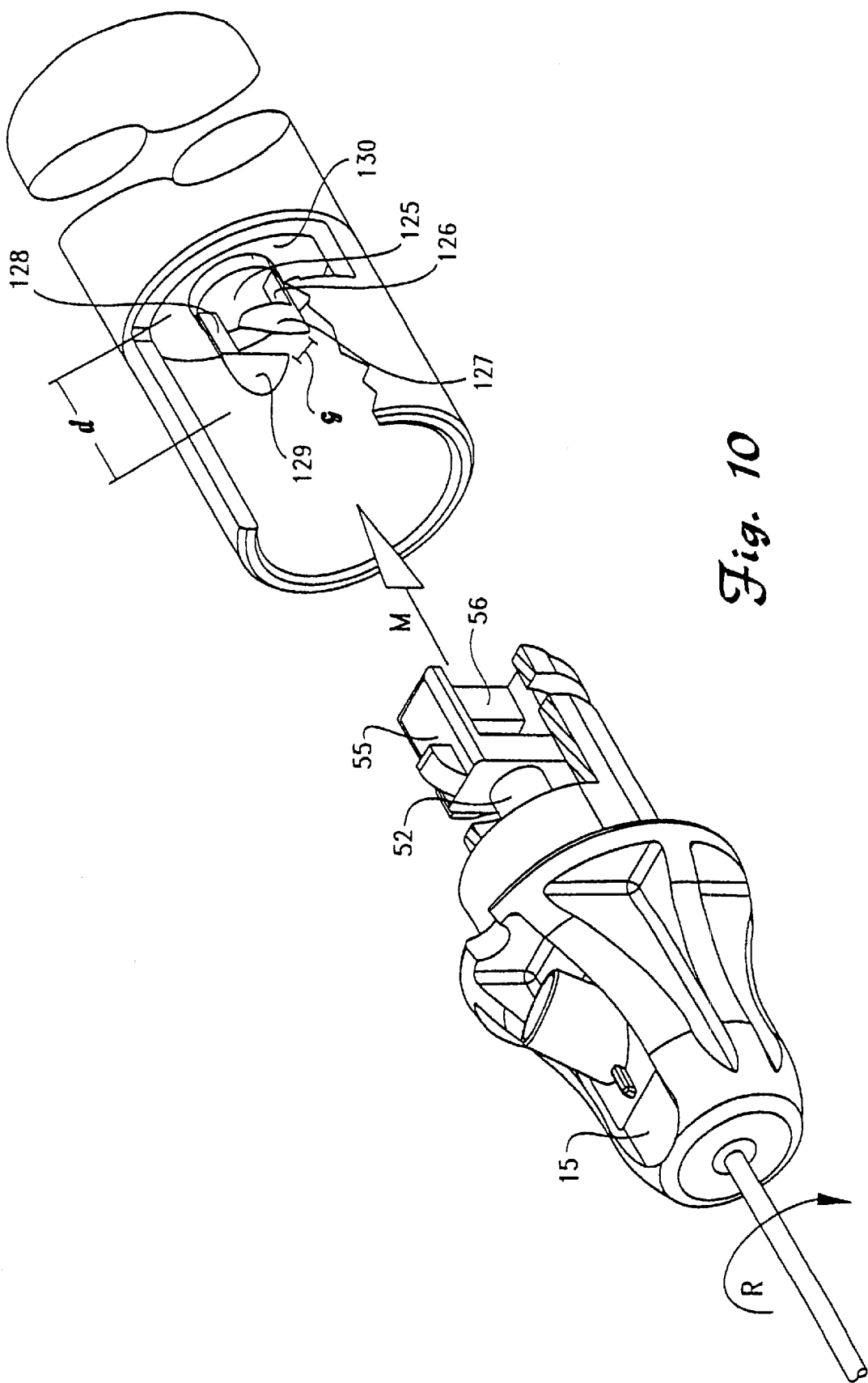
FIG. 10 is a partial sectional exploded view of the cutter assembly shown in FIG. 1.

Referring now to FIGS. 2 and 10, the surgical cutting instruments 10 of this invention include a drive connector 120 disposed within the chamber 70 of the hub connector 60.

Other arrangements are contemplated so long as the drive connector 120 is matable to the mating portion 55 of the drive element 50 when the hub 15 is engaged to the hub connector 60. The drive connector 120 is operably engageable to the source of motion. The mating portion 55 of the drive element 50 and the drive connector 120 will be complementary so that the disposable assembly can be releasably matable. In a preferred embodiment where the mating portion 55 includes a transverse bar 56, the drive connector 120 includes a bayonet element 125 that is releasably matable to the transverse bar. As shown in FIG. 10, the bayonet element 125 includes a pair of spaced arms 126, 128 each terminating in a hook 127, 129. The bayonet element 125 is configured to releasably receive the transverse bar 56 when the hub 15 is disposed within the chamber 70 of the hub connector 60 and the lock member 22 is received within the longitudinal section 76 of the channel 75. The bayonet element 125 will capture the transverse bar 56 when the hub 15 is rotated in the direction of arrow R so that the locking member 22 of the hub 15 is disposed within the locking recess 81.

Figure 11:
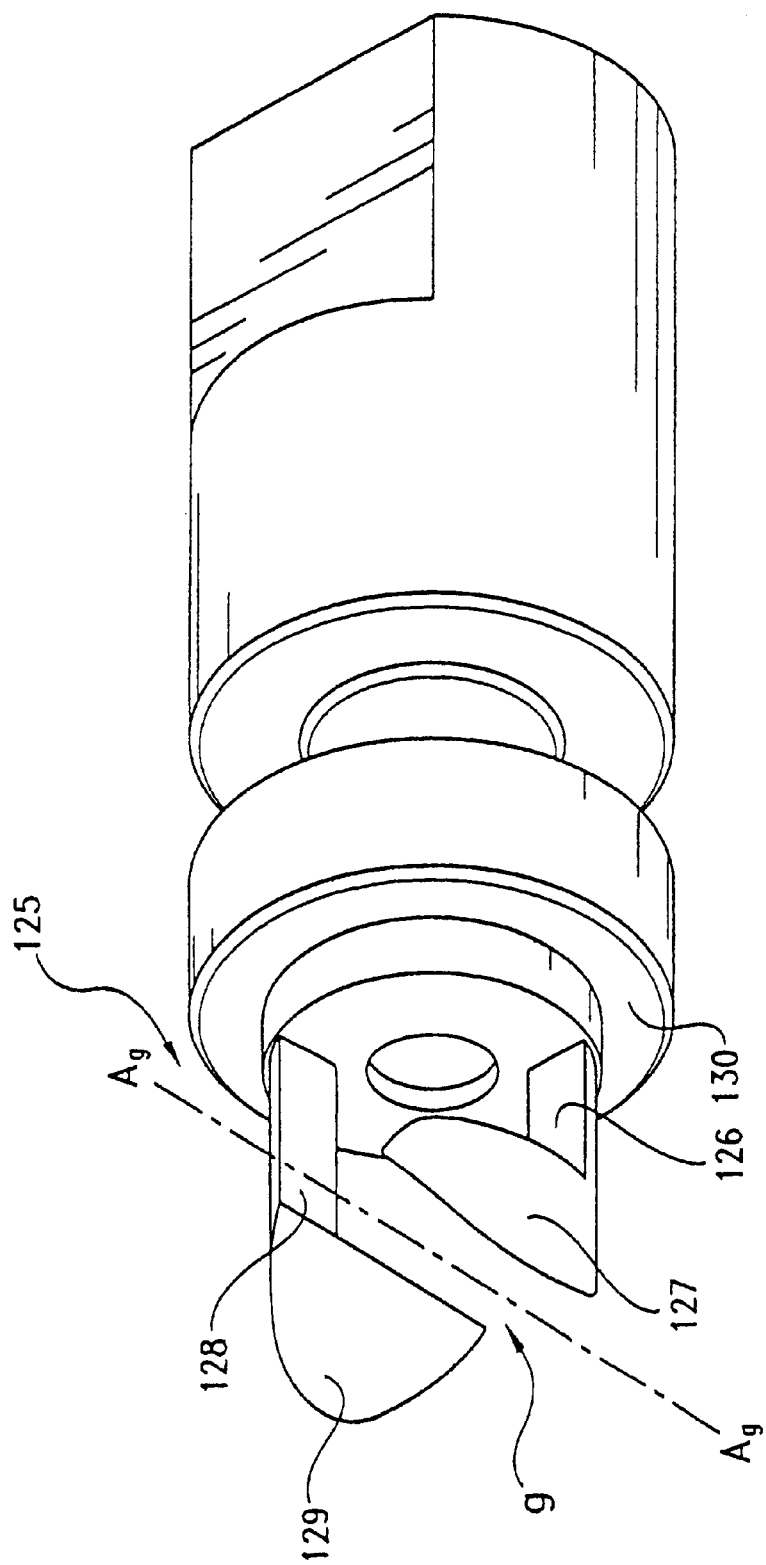
FIG. 11 is a side elevational view of a drive connector according to one embodiment of the present invention.

As shown in FIGS. 10 and 11, the arms 126, 128 are preferably spaced and parallel to form a gap g between the hooks 127, 129. The gap g has a longitudinal axis $A_g$. The gap is sized for releasably receiving the transverse bar 56 when the bar 56 is disposed within the gap g with the length $l_b$ (FIG. 4) of the bar 56 along the longitudinal axis $A_g$ of the gap g. The bayonet element 125 of this invention preferably is provided with a spring platform 130 adjacent the bayonet element 125 and spaced from the hooks 127, 129 at a spring loaded distance d for the spring element The instruments of this invention also include various features to facilitate the excision of tissue. For example, an aspiration tube 140 is disposed within a slot 27 defined in the hub 15. The aspiration tube 140 is connected to a suitable vacuum source and tissue collection chamber in a manner well known in the art.

The devices of this invention are made from any suitable material, preferably an economical material that makes single use of the disposable components economically feasible. For example, the hubs 15, spring elements 100 and drive mechanisms are preferably formed of molded plastic. In a preferred embodiment, the molded plastic is polycarbonate, or the like. However, any suitable plastic that is sterilization compatible and structurally stable is contemplated. The needles 30, 35 are preferably composed of surgical grade stainless steel.

The devices will also have suitable sizes for the intended application For ophthalmic surgeries, in one embodiment; the outer cannula 30 had a length of 1.220 inches from the proximal end 32 to the distal end 33 with a total length of 1.335 inches with a diameter of about 0.050 inches or less. The inner cutter 35 had a length of 1.941 inches from the operational end 36 to the engagement end 38 with a diameter of about 0.040 inches. The drive element 50 had a maximum width of 0.315 inches including the projections 51 and a minimum width of 0.226 inches and a height of 0.047 inches. The drive spring 13 had an outer diameter of 0.170 inches. The hub 15 had a length of about 1.01 including the beam spring 100 and each boss 105 was about 0.025 inches. The lock member 22 had a height of about 1 mm. Each beam 101 had a length of about 0.041 inches separated by a 0.050 inch cut-away from the hub body 15. The major diameter of the hub 15 was 0.510 inches.

The present invention provides disposable surgical cutting assemblies that can be used with powered hand-pieces that are commercially available. The assemblies of this invention provide an elegant connection mechanism that requires minimal components thus reducing the risk of device malfunction and preventing incorrect connection of the blade to the power source. Proper connection of the disposable component is also assured because all of the moving parts of the assembled surgical cutting instrument are contained within the disposable component.

While the invention has been illustrated and described in detail in the drawings and foregoing description, the same is to be considered as illustrative and not restrictive in character. It should be understood that only the preferred embodiments have been shown and described and that all changes and modifications that come within the spirit of the invention are desired to be protected.

What is claimed is:

1. A surgical cutting instrument, comprising:

a hollow hub having a working portion terminating at a working end and a connection portion terminating at a connection end, said connection portion defining a cavity and having a lock member projecting from an outer surface of said connection portion, an outer tubular member having a length sized for insertion into an anatomical space, said outer tubular member defining a central bore along said length of said outer tubular member, said outer tubular member having a proximal end attached to said working end of said hub and a distal end, said outer tubular member defining a cutting opening adjacent said distal end and sized to receive tissue therethrough;

a cutting member slidably disposed within said central bore of said outer tubular member, said cutting member having a first operational end defining a cutting head and a second engagement end disposed proximal to said cavity of said hub;

a powered hand-piece including a source of motion and an outer shell defining an outer gripping portion;

a hollow hub connector having a length and a cylindrical wall with a hand-piece connection portion and a hub engagement portion, said hand-piece connection portion disposed within the hand-piece, said hub engagement portion defining a chamber for receiving said connection portion of said hub, said chamber having a longitudinal axis parallel to said length, said hub engagement portion further defining a channel through said cylindrical wall for receiving said lock member, said channel in communication with said chamber and having, a longitudinal section defined along the length of said hub connector, a second transverse section communicating with said longitudinal section at a first end and having a second opposite end, a locking recess defined in said wall perpendicularly to said transverse section and in communication with said opposite end of said transverse section, said locking recess sized to receive said lock member, whereby said connection portion of said hub is slidable within said chamber along said longitudinal axis when said lock member is disposed within said longitudinal section of said channel and said connection portion of said hub is rotatable within said chamber when said lock member is disposed within said transverse section of said channel and said connection portion of said hub fixed within said chamber when said lock member is disposed within said locking recess; and a spring element disposed on said connection portion of said hub, said spring element configured to urge said lock member into said locking recess when said lock member is rotated into said opposite end of said transverse section of said channel, said spring element having a squeezed position when said lock member is in said transverse section of said channel and a substantially at rest position when said lock members is in said locking recess, said spring element being a beam spring disposed at the connection end of said hub, said beam spring including a beam having a first surface facing said connection end and a second opposite face.

2. The instrument of claim 1, wherein said spring element further comprises a boss projecting from said opposite face of said beam.

3. A surgical cutting instrument, comprising:

a hollow hub having a working portion terminating at a working end and a connection portion terminating at a connection end, said connection portion defining a cavity and having a lock member projecting from an outer surface of said connection portion;

an outer tubular member having a length sized for insertion into an anatomical space, said outer tubular member defining a central bore alone said length of said outer tubular member, said outer tubular member having a proximal end attached to said working end of said hub and a distal end, said outer tubular member defining a cutting opening adjacent said distal end and sized to receive tissue therethrough, said cutting opening defining a cutting edge thereon;

a cutting member slidably disposed within said central bore of said outer tubular member, said cutting member having a first operational end defining a cutting head and a second engagement end disposed proximal to said cavity of said hub;

a powered hand-piece including a source of motion and an outer shell defining an outer gripping portion;

a hollow hub connector having a length and a cylindrical wall with a hand-piece connection portion and a hub engagement portion, said hand-piece connection portion disposed within the hand-piece, said hub engagement portion defining a chamber for receiving said connection portion of said hub, said chamber having a longitudinal axis parallel to said length, said hub engagement portion further defining a channel through said cylindrical wall for receiving said lock member, said channel in communication with said chamber and having, a longitudinal section defined alone the length of said hub connector, a second transverse section communicating with said longitudinal section at a first end and having a second opposite end, a locking recess defined in said wall perpendicularly to said transverse section and in communication with said opposite end of said transverse section, said locking recess sized to receive said lock member, whereby said connection portion of said hub is slidable within said chamber alone said longitudinal axis when said lock member is disposed within said longitudinal section of said channel and said connection portion of said hub is rotatable within said chamber when said lock member is disposed within said transverse section of said channel and said connection portion of said hub fixed within said chamber when said lock member is disposed within said locking recess;

a spring element disposed on said connection portion of said hub body, said spring element configured to urge said lock member into said locking recess when said lock member is rotated into said opposite end of said transverse section of said channel, said spring element having a squeezed position when said lock member is in said transverse section of said channel and a substantially at rest position when said lock member is in said locking recess.

said spring element being a beam spring disposed at the connection end of said hub body, said beam spring including a beam having a first surface facing said connection end and a second opposite face; and a drive element disposed within said cavity and having a drive mount portion connected to said engagement end of said cutting member and a mating portion operationally connectable to the source of motion when said hub is operationally engaged to the hand-piece, said drive element translating motion from the source of motion to said cutting member to move said cutting member relative to said outer tubular member so said cutting edge of said cutting opening traverses said cutting head, said drive element including a drive connector disposed within said chamber and releasably matable to said mating portion of said drive element when said hub is engaged to said hub connector, said drive connector operatively engageable to the source of motion, said mating portion including a transverse bar disposed within said cavity of said hub and said drive connector including a bayonet element matable to said transverse bar, said bayonet element having a pair of spaced arms each terminating in a hook, said bayonet element configured to releasably receive said transverse bar when said hub is disposed within said chamber and said lock member is received within said longitudinal channel and capture said transverse bar when said hub is rotated so that the lock member of said hub is disposed within said locking recess.

4. The instrument of claim 3 wherein said arms are spaced and parallel to form a gap having a longitudinal axis, between said hooks, for releasably receiving said bar when said bar is disposed within said gap with said length of said bar along said longitudinal axis of said gap.

5. The instrument of claim 3 wherein said drive connector defines a spring platform adjacent said bayonet element and spaced from said hooks at a spring-loaded distance for said beam spring.

6. A hub for a disposal surgical cutting assembly having an outer tubular member and an inner cutting member operationally engagable to a powered hand-piece, comprising:

a hollow hub body configured to slidably receive the cutting member therethrough and configured to support the outer tubular member having a working portion terminating at a working end and a connection portion terminating at a connection end, said connection portion having a lock member projecting from an outer surface thereof;

a hollow hub connector having a length and a cylindrical wall with a hand-piece connection portion and a hub engagement portion, said connection portion disposable within the hand-piece, said hub engagement portion defining a chamber for receiving said connection portion of said hub body, said hub engagement portion further defining a channel through said cylindrical wall for receiving said lock member, said channel in communication with said chamber and having,
  a longitudinal section defined alone the length of said hub connector,
  a second transverse section communicating with said longitudinal section at a first end and having a second opposite end,
  a locking recess defined in said wall perpendicularly to said transverse section and in communication with said opposite end of said transverse section.
said locking recess sized to receive said lock member,
whereby said connection portion of said hub body is slidable within said chamber when said lock member is disposed within said longitudinal section of said channel and said connection portion of said hub body is rotatable within said chamber when said lock member is disposed within said transverse section of said channel and said connection portion of said hub body fixed within said chamber when said lock member is disposed within said locking recess; and
a spring element disposed on said connection portion of said hub body, said spring element configured to urge said lock member into said locking recess when said lock member is rotated into said opposite end of said transverse section of said channel,
said spring element having a squeezed position when said lock member is in said transverse section of said channel and a substantially at rest position when said lock member is in said locking recess,
said spring element being a beam spring disposed at the connection end of said hub body, said beam spring including a beam having a first surface facing said connection end and a second opposite face.

7. The hub of claim 6, wherein said spring element further comprises a boss projecting from said opposite face of said beam.

8. A disposable surgical cutting assembly for operationally engaging a powered hand-piece, comprising:
  a hollow hub having a working portion terminating at a working end and a connection portion terminating at a connection end, said connection portion defining a cavity, said connection portion having a lock member projecting from an outer surface of said connection portion for engaging a locking groove disposed within the hand-piece;
  a beam spring disposed on the connection end of said hub, said beam spring including a first beam having a first surface facing said connection end and a second opposite face for acting against a spring platform disposed within the hand-piece to urge said lock member into the locking recess in the hand-piece;
  an outer tubular member sized for insertion into an anatomical space, said outer tubular member defining a central bore along the length of said outer tubular member, said outer tubular member having a proximal end attached to said working end of said hub and a distal end, said outer tubular member defining a cutting opening having a first cutting edge adjacent said distal end and sized to receive tissue therethrough;
  a cutting member slidably disposed within said central bore of said outer tubular member, said cutting member having a first operational end defining a cutting head having a second cutting edge and a second engagement end disposed within said cavity of said hub;
  a drive element disposed within said cavity and having a drive mount portion connected to said engagement end of said cutting member and a mating portion operationally connectable to a source of motion when said hub is operationally engaged to the hand-piece, said drive element translating motion from the source of motion to said cutting member to move said cutting member relative to said outer tubular member so said second cutting edge traverses said first cutting edge.

9. The assembly of claim 8 further comprising a boss projecting from said opposite face of said first beam.

10. The assembly of claim 8 wherein said beam spring further includes a second beam disposed on said connection end of said hub spaced from said first beam, said second beam spring having a first surface facing said connection end and a second opposite face for cooperating with said first beam in acting against a spring platform disposed within the hand-piece to urge said lock member into the locking recess in the hand-piece.

11. The assembly of claim 10 further comprising a boss projecting from said opposite face of each of said first and second beams.

* * * * *

UNITED STATES PATENT AND TRADEMARK OFFICE
CERTIFICATE OF CORRECTION

PATENT NO. : 6,494,892 B1
DATED : December 17, 2002
INVENTOR(S) : Ireland et al.

It is certified that error appears in the above-identified patent and that said Letters Patent is hereby corrected as shown below:

Column 9,
Line 9, delete "members" and add -- member --
Lines 25, 50 and 60, delete "alone" and add -- along --

Column 11,
Line 5, delete "alone" and add -- along --

Signed and Sealed this

Seventeenth Day of June, 2003

JAMES E. ROGAN
*Director of the United States Patent and Trademark Office*